United States Patent
Zhou et al.

(10) Patent No.: US 12,217,848 B2
(45) Date of Patent: Feb. 4, 2025

(54) METHOD AND APPARATUS FOR ADAPTIVE RADIATION THERAPY BASED ON PLAN LIBRARY INVOKING

(71) Applicant: MANTEIA TECHNOLOGIES CO., LTD., Fujian (CN)

(72) Inventors: Qichao Zhou, Fujian (CN); Zirong Li, Fujian (CN)

(73) Assignee: MANTEIA TECHNOLOGIES CO., LTD., Fujian (CN)

(*) Notice: Subject to any disclaimer, the term of this patent is extended or adjusted under 35 U.S.C. 154(b) by 339 days.

(21) Appl. No.: 17/746,892

(22) Filed: May 17, 2022

(65) Prior Publication Data

US 2023/0260624 A1 Aug. 17, 2023

(30) Foreign Application Priority Data

Feb. 11, 2022 (CN) .......................... 202210130585.3

(51) Int. Cl.
*G16H 20/00* (2018.01)
*A61B 6/00* (2006.01)
(Continued)

(52) U.S. Cl.
CPC ........... *G16H 20/40* (2018.01); *A61B 6/5229* (2013.01); *G16H 10/60* (2018.01); *G16H 30/40* (2018.01); *G16H 50/20* (2018.01)

(58) Field of Classification Search
CPC ........ G16H 20/40; G16H 10/60; G16H 50/20; G16H 30/40; A61B 6/5229
See application file for complete search history.

(56) References Cited

U.S. PATENT DOCUMENTS

| | | | |
|---|---|---|---|
| 11,648,418 B2* | 5/2023 | Owens | A61N 5/1031 378/65 |
| 2016/0140300 A1* | 5/2016 | Purdie | G16H 20/40 705/2 |

(Continued)

FOREIGN PATENT DOCUMENTS

| | | | |
|---|---|---|---|
| CN | 106920234 A | 7/2017 | |
| CN | 108744313 A * | 11/2018 | ........... A61N 5/1031 |

(Continued)

OTHER PUBLICATIONS

The EESR of family EP application No. 22175767.7 issued on Nov. 11, 2022.

(Continued)

*Primary Examiner* — Khai M Nguyen
(74) *Attorney, Agent, or Firm* — Samson G. Yu

(57) ABSTRACT

This application discloses a method and apparatus for Adaptive Radiation Therapy (ART) based on plan library invoking. The method includes: acquiring a medical image of the day and a target plan library of a target patient, where the target plan library includes a plurality of groups of images of the target patient and a radiation therapy plan corresponding to each set of images; and determining the radiation therapy plan corresponding to the target patient according to the medical image of the day and the target plan library. According to this application, a problem that high-speed ART cannot be achieved due to excessive time consumption during the designing of the radiation therapy plan in the related art is resolved.

9 Claims, 5 Drawing Sheets

(51) Int. Cl.
*G16H 10/60* (2018.01)
*G16H 20/40* (2018.01)
*G16H 30/40* (2018.01)
*G16H 50/20* (2018.01)

(56) References Cited

U.S. PATENT DOCUMENTS

| | | |
|---|---|---|
| 2018/0211725 A1* | 7/2018 | Purdie .................... G16H 10/60 |
| 2019/0232087 A1 | 8/2019 | Cordero Marcos et al. |
| 2020/0038683 A1 | 2/2020 | Schadewaldt et al. |
| 2021/0031054 A1* | 2/2021 | Ranganathan ......... G16H 50/20 |

FOREIGN PATENT DOCUMENTS

| | | | |
|---|---|---|---|
| CN | 109771850 A | * | 5/2019 |
| CN | 111481839 A | | 8/2020 |

OTHER PUBLICATIONS

The first office action of family CN application No. 202210130585.3 issued on Jun. 2, 2023.

\* cited by examiner

METHOD AND APPARATUS FOR ADAPTIVE RADIATION THERAPY BASED ON PLAN LIBRARY INVOKING

TECHNICAL FIELD

This application relates to the technical field of radiation therapy, and specifically, to a method and apparatus for Adaptive Radiation Therapy (ART) based on plan library invoking.

BACKGROUND

Currently, radiation therapy plays an increasingly important role in the treatment of cancer patients. A course of radiation therapy usually takes a month or more. A radiation therapy plan is generated according to initial positioning images of a patient before radiation therapy begins. However, the location and the shape of the tumor of the patient often change throughout the course of radiation therapy, which may lead to possible deviations in radiation dose during radiation therapy, so that not only a radiation therapy effect is affected, but also the normal organs and tissues of the patients are further affected, resulting in complications. Adaptive Radiation Therapy (ART) achieves the online updating of a treatment plan based on movement changes in human body tissues, to cause the whole course of radiation therapy from diagnosis, plan design, and treatment implementation to verification to become a self-adaptive and self-correcting dynamic closed-loop system, to achieve high-precision radiotherapy and cause an actual irradiation situation to approach to an actual state. Currently, there are usually three manners to achieve ART: Offline Adaptive Radiation Therapy (Offline ART), Online Adaptive Radiation Therapy (Online ART), and Real time Adaptive Radiation Therapy (Real-time ART). The Offline ART is usually used for correcting a treatment plan. However, the Offline ART method currently uses a conventional commercial treatment plan system, which is low in efficiency, and time and labor consuming, so the method is rarely adopted by hospitals. The Online ART acquires an anatomical structure image of the patient before a certain fractionated treatment of the patient and then rapidly generates a new treatment plan for the patient. The Real-time ART may adjust the treatment plan in real time during the irradiation of each treatment fraction of the patient. That an Online ART plan currently used cannot be widely used in actual clinical treatment mainly has the following problems and disadvantages. When generating the new treatment plan, the Online ART needs to calculate and solve radiation doses. Calculation time is very long, and cannot be completed within a clinically acceptable time. In addition, the Online ART method requires doctors and physicists to participate in the optimization process of the whole course of the radiation therapy plan. It also needs a long time to set and adjust parameters manually. The quality of the treatment plan is also directly limited by the experience and determination of the doctors and the physicists.

Given the problem that high-speed ART cannot be achieved due to excessive time consumption during the designing of the radiation therapy plan in the related art, no effective solution has been proposed yet.

SUMMARY

This application is mainly intended to provide a method and apparatus for Adaptive Radiation Therapy (ART) based on a plan library invoking, to resolve a problem that high-speed ART cannot be achieved due to excessive time consumption during the designing of the radiation therapy plan in the related art.

In order to realize the above purpose, an aspect of this application provides a method for ART. The method includes: acquiring a medical image of the day and a target plan library of a target patient, where the target plan library includes a plurality of groups of images of the target patient and a radiation therapy plan corresponding to each set of images; and determining the radiation therapy plan corresponding to the target patient according to the medical image of the day and the target plan library.

Further, the acquiring a medical image of the day and a target plan library of a target patient includes: determining whether there is an offline plan library corresponding to the target patient, where the offline plan library comprises a plurality of groups of images of the target patient and a radiation therapy plan corresponding to each set of images; when there is the offline plan library corresponding to the target patient, performing image registration on the medical image of the day and the plurality of groups of images in the offline plan library to obtain a deformation field; and when a deformation quantity of the deformation field is less than a preset threshold I, using the offline plan library as the target plan library, or updating the radiation therapy plan of the offline plan library according to the deformation quantity to obtain the target plan library.

Further, the method includes: when there is no offline plan library corresponding to the target patient, or the deformation quantity of the deformation field is greater than or equal to the preset threshold I, constructing the target plan library of the target patient based on a data set of the medical image of the day.

Further, the construction of the target plan library of the target patient based on a data set of the medical image of the day includes: acquiring the plurality of groups of images of the target patient from the data set of the medical image of the day; generating an initial radiation therapy plan corresponding to each set of images; and performing checking and verification on the initial radiation therapy plan, and constructing the target plan library by using the checked and verified initial radiation therapy plan.

Further, before the determining the radiation therapy plan corresponding to the target patient according to the medical image of the day and the target plan library, the method further includes: acquiring a motion time sequence data set of the target patient, where the motion time sequence data set includes at least a body surface feature motion time sequence of the target patient or an in vivo feature motion time sequence of the target patient; constructing a trajectory prediction model according to the motion time sequence data set, where the trajectory prediction model is configured to perform trajectory prediction on a region of interest of the target patient; and performing delay correction on the trajectory prediction model to obtain a target trajectory prediction model.

Further, the determining the radiation therapy plan corresponding to the target patient according to the medical image of the day and the target plan library includes: predicting position information of the region of interest after preset time according to the target trajectory prediction model to obtain the predicted position information; acquiring a radiation therapy plan I matching the predicted position information from the target plan library; performing contrastive analysis on the predicted position information and real-time position information of the region of interest to obtain a difference value; and when the difference value is less than a preset threshold II, using the radiation therapy plan I as the radiation therapy plan corresponding to the target patient.

Further, the determining the radiation therapy plan corresponding to the target patient according to the medical image of the day and the target plan library includes: matching the plurality of groups of images in the target plan library according to the medical image of the day to obtain a target image; acquiring a radiation therapy plan corresponding to the target image; and using the radiation therapy plan corresponding to the target image as the radiation therapy plan corresponding to the target patient.

In order to realize the above purpose, another aspect of this application provides an apparatus for ART. The apparatus includes a first acquisition unit and a determination unit. The first acquisition unit is configured to acquire a medical image of the day and a target plan library of a target patient. The target plan library includes a plurality of groups of images of the target patient and a radiation therapy plan corresponding to each set of images. The determination unit is configured to determine the radiation therapy plan corresponding to the target patient according to the medical image of the day and the target plan library.

Further, the acquisition unit includes a determination module, a registration module, and an updating module. The determination module is configured to determine whether there is an offline plan library corresponding to the target patient. The offline plan library includes a plurality of groups of images of the target patient and a radiation therapy plan corresponding to each set of images. The registration module is configured to, when there is the offline plan library corresponding to the target patient, perform image registration on the medical image of the day and the plurality of groups of images in the offline plan library to obtain a deformation field. The updating module is configured to, when a deformation quantity of the deformation field is less than a preset threshold I, use the offline plan library as the target plan library, or update the radiation therapy plan of the offline plan library according to the deformation quantity to obtain the target plan library.

Further, the apparatus includes a first construction unit. The first construction unit is configured to, when there is no offline plan library corresponding to the target patient, or the deformation quantity of the deformation field is greater than or equal to the preset threshold I, construct the target plan library of the target patient based on a data set of the medical image of the day.

Further, the construction unit includes a first acquisition module, a generation module, and an adoption module. The first acquisition module is configured to acquire the plurality of groups of images of the target patient from the data set of the medical image of the day. The generation module is configured to generate an initial radiation therapy plan corresponding to each set of images. The adoption module is configured to perform checking and verification on the initial radiation therapy plan, and construct the target plan library by using the checked and verified initial radiation therapy plan.

Further, the apparatus includes a second acquisition unit, a second construction unit, and a correction unit. The second acquisition unit is configured to, before the radiation therapy plan corresponding to the target patient is determined according to the medical image of the day and the target plan library, acquire a motion time sequence data set of the target patient. The motion time sequence data set includes at least a body surface feature motion time sequence of the target patient or an in vivo feature motion time sequence of the target patient. The second construction unit is configured to construct a trajectory prediction model according to the motion time sequence data set. The trajectory prediction model is configured to perform trajectory prediction on a region of interest of the target patient. The correction unit is configured to perform delay correction on the trajectory prediction model to obtain a target trajectory prediction model.

Further, the determination unit includes a prediction module, a second acquisition module, a comparison module, and a first determination module. The prediction module is configured to predict position information of the region of interest after a preset time according to the target trajectory prediction model to obtain the predicted position information. The second acquisition module is configured to acquire a radiation therapy plan I matching the predicted position information from the target plan library. The comparison module is configured to perform contrastive analysis on the predicted position information and real-time position information of the region of interest to obtain a difference value. The first determination module is configured to, when the difference value is less than a preset threshold II, use the radiation therapy plan I as the radiation therapy plan corresponding to the target patient.

Further, the determination unit includes a matching module, a third acquisition module, and a second determination module. The matching module is configured to match the plurality of groups of images in the target plan library according to the medical image of the day to obtain a target image. The third acquisition module is configured to acquire a radiation therapy plan corresponding to the target image. The second determination module is configured to use the radiation therapy plan corresponding to the target image as the radiation therapy plan corresponding to the target patient.

Another aspect of an embodiment of the present invention further provides a computer-readable storage medium. The storage medium stores a program. When the program is operated, a device where the storage medium is located is controlled to perform any of the above methods for ART based on plan library invoking.

Another aspect of an embodiment of the present invention provides a processor. The processor is configured to operate a program. When the program is operated, any of the above methods for ART based on plan library invoking is performed.

Through this application, the following steps are adopted. The medical image of the day and the target plan library of the target patient are acquired. The target plan library includes a plurality of groups of images of the target patient and a radiation therapy plan corresponding to each set of images. The radiation therapy plan corresponding to the target patient is determined according to the medical image of the day and the target plan library. In this way, the problem that high-speed ART cannot be achieved due to excessive time consumption during the designing of the radiation therapy plan in the related art is resolved. Through the medical image of the day of the target patient and in view of the target plan library of the target patient, the radiation therapy plan of this radiation therapy for the target patient may be directly determined, so that an effect of the high-speed ART for the target patient can be achieved.

BRIEF DESCRIPTION OF THE DRAWINGS

The drawings described herein are used to provide a further understanding of this application and constitute a part of this application. The exemplary embodiments and descriptions of this application are used to explain this application and do not constitute an improper limitation of this application. In the drawings.

DETAILED DESCRIPTION OF THE EMBODIMENTS

It is to be noted that the embodiments in this application and the features in the embodiments may be combined with one another without conflict. This application will now be described below in detail with reference to the drawings and the embodiments.

In order to enable those skilled in the art to better understand the solutions of this application, the technical solutions in the embodiments of this application will be clearly and completely described below in combination with the drawings in the embodiments of this application. It is apparent that the described embodiments are only part of the embodiments of this application, not all the embodiments. All other embodiments obtained by those of ordinary skill in the art on the basis of the embodiments in this application without creative work shall fall within the scope of protection of this application.

It is to be noted that the terms "first", "second" and the like in the description, claims, and the above-mentioned drawings of this application are used for distinguishing similar objects rather than describing a specific sequence or a precedence order. It should be understood that the data used in such a way may be exchanged where appropriate, so that the embodiments of this application described here can be implemented. In addition, the terms "include" and "have" and any variations thereof are intended to cover non-exclusive inclusions. For example, it is not limited to processes, methods, systems, products, or devices containing a series of steps or units to clearly list those steps or units, and other steps or units which are not clearly listed or are inherent to these processes, methods, products or devices may be included instead.

Figure 1:
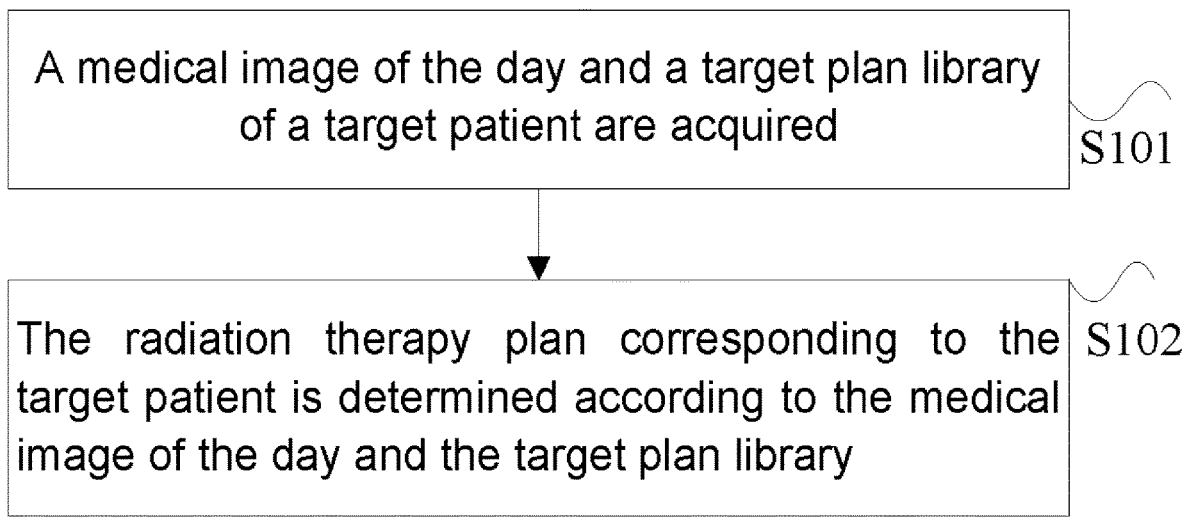
FIG. 1 is a flowchart of a method for ART based on plan library invoking according to an embodiment of this application.

The present invention is described below with reference to preferred implementation steps. FIG. 1 is a flowchart of a method for ART based on plan library invoking according to an embodiment of this application. As shown in FIG. 1, the method includes the following steps.

At step S101, a medical image of the day and a target plan library of a target patient are acquired, and the target plan library includes a plurality of groups of images of the target patient and a radiation therapy plan corresponding to each set of images.

Specifically, before the target patient undergoes current radiation therapy, the scanning of the medical image of the day is first performed on the target patient to obtain the medical image of the day of the target patient, and then the target plan library for the target patient is acquired. The target plan library includes a plurality of groups of images of the target patient and radiation therapy plans corresponding to the plurality of groups of images.

At step S102, the radiation therapy plan corresponding to the target patient is determined according to the medical image of the day and the target plan library.

Specifically, the radiation therapy plan of this radiation therapy for the target patient is obtained according to the medical image of the day and the target plan library of the target patient.

To sum up, the radiation therapy plan of this radiation therapy for the target patient may be accurately obtained through the medical image of the day and the target plan library of the target patient. Therefore, the design time of the target plan library for the target patient can be shortened, and the problem that high-speed ART cannot be achieved due to excessive time consumption during the designing of the radiation therapy plan in the related art can be resolved.

Optionally, in the method for ART based on plan library invoking provided in an embodiment of this application, the acquiring a medical image of the day and a target plan library of a target patient includes: determining whether there is an offline plan library corresponding to the target patient, where the offline plan library comprises a plurality of groups of images of the target patient and a radiation therapy plan corresponding to each set of images; when there is the offline plan library corresponding to the target patient, performing image registration on the medical image of the day and the plurality of groups of images in the offline plan library to obtain a deformation field; and when a deformation quantity of the deformation field is less than a preset threshold I, using the offline plan library as the target plan library, or updating the radiation therapy plan of the offline plan library according to the deformation quantity to obtain the target plan library.

Figure 2:
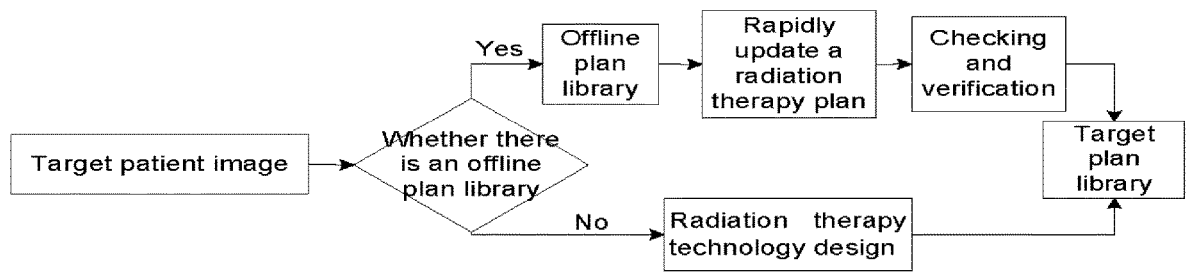
FIG. 2 is a flowchart I of optionally acquiring a target plan library according to an embodiment of this application.

Specifically, acquiring a target plan library includes, as shown in FIG. 2, determining whether there is an offline plan library corresponding to the target patient. The offline plan library is a radiation therapy plan library based on the plurality of groups of images of the target patient without radiation therapy. When there is the offline plan library, registration is performed on the medical image of the day of the target patient and the plurality of groups of images in the offline plan library. Image registration is performed to obtain the deformation field. The deformation quantity of the deformation field can accurately reflect a difference quantity between the medical image of the day and the plurality of groups of images in the offline plan library. Therefore, when the deformation quantity is less than the preset threshold I, the offline plan library is directly used as the target plan library. Alternatively, the radiation therapy plan in the offline plan library is updated and adjusted according to the current deformation quantity, to obtain the target plan library.

Through the above steps, the radiation therapy plan of the offline plan library is updated according to the medical image of the day of the target patient to obtain the target plan library, so that changes in tissues in the target patient are fully considered and corrected. Therefore, accurate radiation therapy for the target patient can be guaranteed. It is to be noted that, all of the radiation therapy plans are required to be checked and verified, that is, Quality Assurance (QA) verification.

Optionally, in the method for ART based on plan library invoking provided in an embodiment of this application, the method further includes: when there is no offline plan library corresponding to the target patient, or the deformation quantity of the deformation field is greater than or equal to the preset threshold I, constructing the target plan library of the target patient based on a data set of the medical image of the day.

Specifically, when the deformation quantity of the deformation field is greater than or equal to the preset threshold I, or there is no offline plan library, the target plan library is established according to the medical image of the day of the target patient. When the deformation quantity of the deformation field is greater than or equal to the preset threshold I, it indicates that there are relatively large changes in the tissues in the target patient, and the radiation therapy plan in the offline plan library is not applicable to the target patient, so that the target plan library is required to be constructed according to the data set of the medical image of the day.

The radiation therapy plan for the target patient can be accurately updated and optimized through the determination of the deformation quantity, thereby enhancing the quality of the radiation therapy for the target patient.

Optionally, in the method for ART based on plan library invoking provided in an embodiment of this application, the constructing the target plan library of the target patient based on a data set of the medical image of the day includes: acquiring the plurality of groups of images of the target patient from the data set of the medical image of the day; generating an initial radiation therapy plan corresponding to each set of images; and performing checking and verification on the initial radiation therapy plan, and constructing the target plan library by using the checked and verified initial radiation therapy plan.

Figure 3:
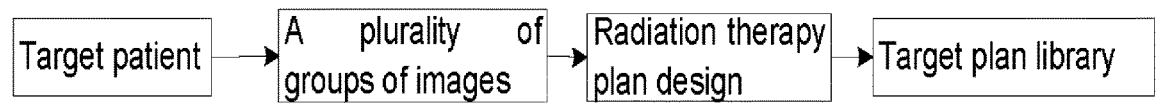
FIG. 3 is a flowchart II of optionally acquiring a target plan library according to an embodiment of this application.

Specifically, the flow of constructing the target plan library according to the medical image of the day is shown in FIG. 3. The plurality of groups of images of the target patient are first acquired. These images may be positioning images. The positioning images include, but are not limited to, 4D images (such as 4DCT and 4DMR), a plurality of positioning CT, and the like. The corresponding initial radiation therapy plan is formulated for each set of images. Then the initial radiation therapy plan is checked and verified. The checked and verified initial radiation therapy plans for the target plan library. The checking and verification may adopt manual checking and verification, or may adopt automatic checking and verification. It is to be noted that, before the radiation therapy plan is formulated, target regions and organs at risk may be automatically or manually delineated for each set of images.

Through the above steps, the target plan library of the target patient is constructed. In this way, when radiation therapy is performed on the target patient later, the radiation therapy plan applicable to the target patient may be directly invoked, so that the efficiency of acquiring the radiation therapy plans can be enhanced.

Optionally, in the method for ART based on plan library invoking provided in an embodiment of this application, before the determining the radiation therapy plan corresponding to the target patient according to the medical image of the day and the target plan library, the method further includes: acquiring a motion time sequence data set of the target patient, where the motion time sequence data set includes at least a body surface feature motion time sequence of the target patient or an in vivo feature motion time sequence of the target patient; constructing a trajectory prediction model according to the motion time sequence data set, where the trajectory prediction model is configured to perform trajectory prediction on a region of interest of the target patient; and performing delay correction on the trajectory prediction model to obtain a target trajectory prediction model.

Figure 4:
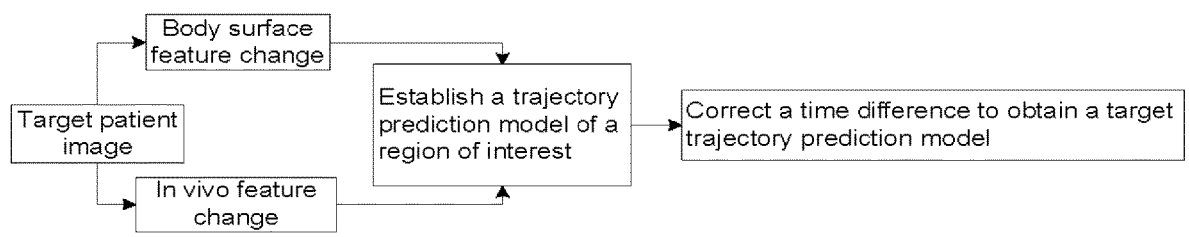
FIG. 4 is a flowchart of optionally acquiring a target trajectory prediction model according to an embodiment of this application.

Specifically, before the radiation therapy plan corresponding to the target patient is determined, the trajectory prediction model is constructed. FIG. 4 is a flowchart of constructing a trajectory prediction model. Before treatment for the target patient on the day begins, the motion time sequence data set of the tissues in the target patient may be acquired according to the plurality of groups of images of the target patient, or the motion time sequence data set is acquired through other manners. Then, according to the motion time sequence data set, the trajectory prediction model of the region of interest is established by using a neural network or a traditional algorithm. After the trajectory prediction model is obtained, delay correction is required to be performed, to ensure that the trajectory prediction model can accurately predict a position of the region of interest. It is to be noted that, before the trajectory prediction model of the region of interest is established, the delineation of the region of interest for the plurality of groups of images may be first automatically or manually performed.

To sum up, the trajectory prediction model of the region of interest of the target patient is established according to features of motion changes in body surface and/or in vivo organ of the target patient. In the flow of ART, the trajectory prediction model may predict the changes in the region of interest of the target patient in advance and match and invoke an execution plan that meets requirements from the target plan library. Therefore, the efficiency of acquiring the radiation therapy plan can be enhanced.

Optionally, in the method for ART based on plan library invoking provided in an embodiment of this application, the determining the radiation therapy plan corresponding to the target patient according to the medical image of the day and the target plan library includes: predicting position information of the region of interest after preset time according to the target trajectory prediction model to obtain the predicted position information; acquiring a radiation therapy plan I matching the predicted position information from the target plan library; performing contrastive analysis on the predicted position information and real-time position information of the region of interest to obtain a difference value; and when the difference value is less than a preset threshold II, using the radiation therapy plan I as the radiation therapy plan corresponding to the target patient.

Specifically, position information of the region of interest after preset time is first predicted according to the target trajectory prediction model, that is, where the region of interest changes to after the preset time elapses. A radiation therapy plan I that meets requirements is matched and invoked from the target plan library according to the predicted position information. It is to be noted that, the radiation therapy plan I includes a plurality of radiation therapy sub-plans. Then, contrastive analysis is performed on the predicted position information and real-time position information. When a difference value between the predicted position information and the real-time position information is less than the preset threshold II, the radiation therapy plan I is used as the radiation therapy plan of this radiation therapy for the target patient. In addition, during the radiation therapy of the target patient, a treatment plan of the target patient may be adjusted in real time according to a predicted position and a real-time position. After radiation therapy is performed on the target patient, treatment situations on the day of image verification of an Electronic Portal Imaging Device (EPID) may be collected.

Through the above steps, the trajectory prediction model may predict the changes in the region of interest of the target patient in advance and match and invoke an execution plan that meets requirements from the target plan library. Therefore, the efficiency of acquiring the radiation therapy plan can be enhanced.

Optionally, in the method for ART based on plan library invoking provided in an embodiment of this application, the determining the radiation therapy plan corresponding to the target patient according to the medical image of the day and the target plan library includes: matching the plurality of groups of images in the target plan library according to the medical image of the day to obtain a target image; acquiring a radiation therapy plan corresponding to the target image; and using the radiation therapy plan corresponding to the target image as the radiation therapy plan corresponding to the target patient.

Specifically, in addition to the determination of the radiation therapy plan of this radiation therapy for the target patient by using the target trajectory prediction model, the following manners may further be adopted. The medical image of the day of the target patient is directly matched with the plurality of groups of images in the target plan library, to obtain a target image that is most similar to the medical image of the day. Then, a radiation therapy plan corresponding to the target image is invoked from the target plan library, and the radiation therapy plan is used as the radiation therapy plan of the target patient.

According to the method for ART based on plan library invoking provided in an embodiment of this application, the medical image of the day and the target plan library of the target patient are acquired. The target plan library includes a plurality of groups of images of the target patient and a radiation therapy plan corresponding to each set of images. The radiation therapy plan corresponding to the target patient is determined according to the medical image of the day and the target plan library. In this way, the problem that high-speed ART cannot be achieved due to excessive time consumption during the designing of the radiation therapy plan in the related art is resolved. Through the medical image of the day of the target patient and in view of the target plan library of the target patient, the radiation therapy plan of this radiation therapy for the target patient may be directly determined, so that an effect of the high-speed ART for the target patient can be achieved.

Figure 5:
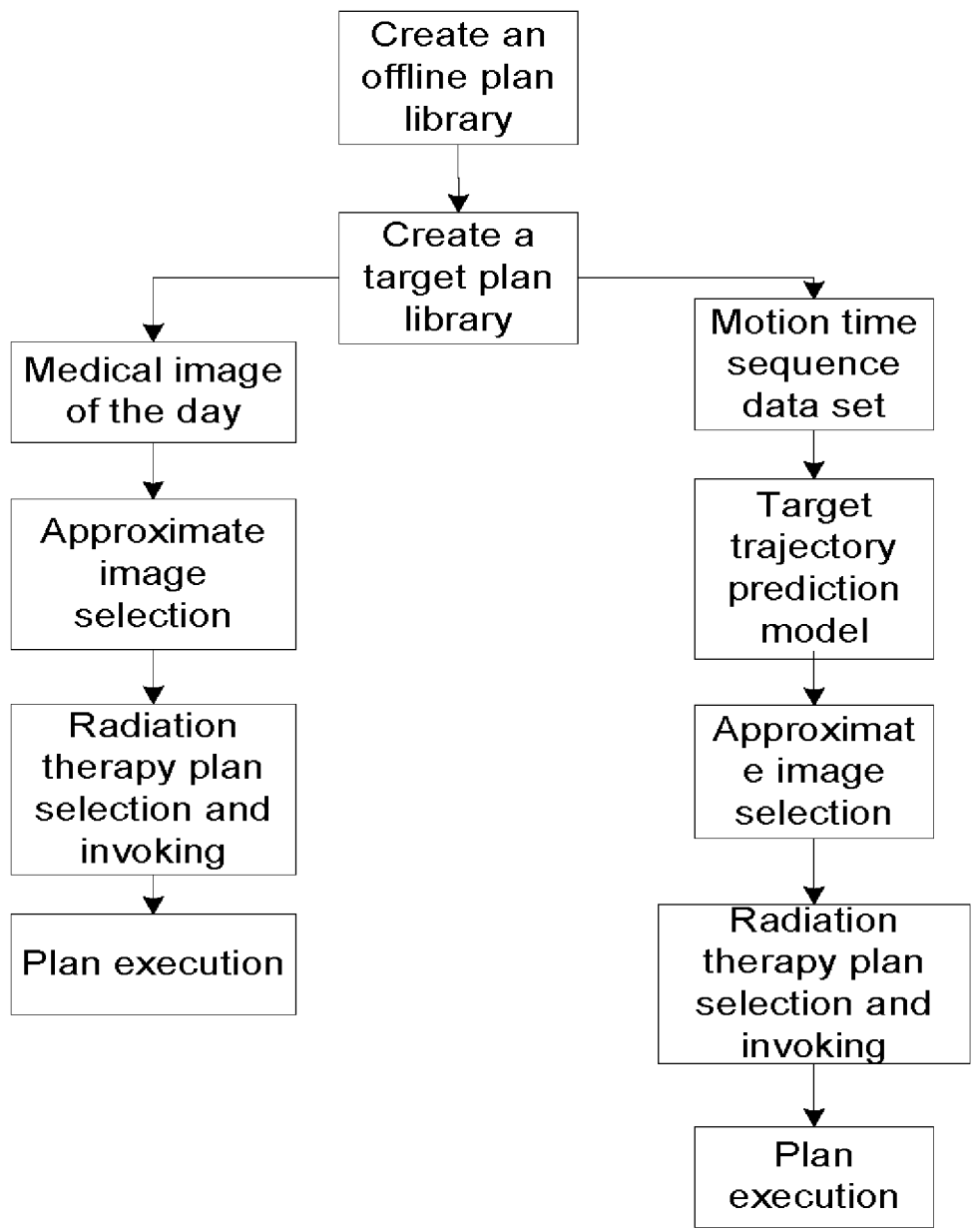
FIG. 5 is a flowchart of an optional method for ART based on plan library invoking according to an embodiment of this application.

FIG. 5 is a flowchart of an optional method for ART based on plan library invoking according to an embodiment of this application. The offline plan library and the target plan library are constructed, and the radiation therapy plan of the target patient is determined. The determination of the radiation therapy plan of the target patient is divided into two manners. In manner I, the medical image of the day of the target patient is matched with the plurality of groups of images in the target plan library, to obtain the target image that is most similar to the medical image of the day; and then, the radiation therapy plan corresponding to the target image is invoked from the target plan library, and the radiation therapy plan is used as the radiation therapy plan of the target patient, to perform the radiation therapy plan. In manner II, the target trajectory prediction model of the region of interest of the target patient is constructed, the position information of the region of interest after the preset time is predicted according to the target trajectory prediction model, and the radiation therapy plan that meets requirements is matched and invoked from the target plan library according to the predicted position information, to perform the radiation therapy plan.

It is to be noted that the steps shown in the flow diagram of the accompanying drawings may be executed in a computer system, such as a set of computer-executable instructions, and although a logical sequence is shown in the flow diagram, in some cases, the steps shown or described may be executed in a different order than here.

An embodiment of this application further provides an apparatus for ART based on plan library invoking. It is to be noted that, the apparatus for ART based on plan library invoking in this embodiment of this application may be configured to perform the method for ART based on plan library invoking provided in the embodiments of this application. The apparatus for ART based on plan library invoking provided in the embodiment of this application is introduced below.

Figure 6:
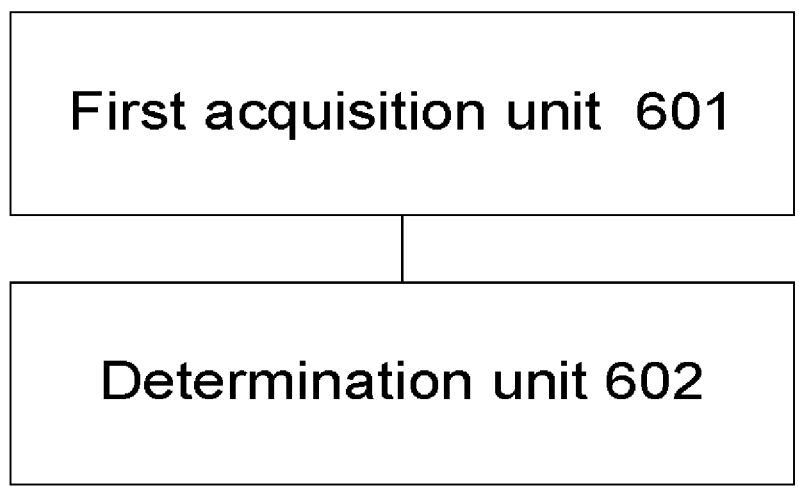
FIG. 6 is a schematic diagram of an apparatus for ART based on plan library invoking according to an embodiment of this application.

FIG. 6 is a schematic diagram of an apparatus for ART based on plan library invoking according to an embodiment of this application. As shown in FIG. 6, the apparatus includes a first acquisition unit 601 and a determination unit 602.

The first acquisition unit 601 is configured to acquire a medical image of the day and a target plan library of a target patient. The target plan library includes a plurality of groups of images of the target patient and a radiation therapy plan corresponding to each set of images.

The determination unit 602 is configured to determine the radiation therapy plan corresponding to the target patient according to the medical image of the day and the target plan library.

According to the apparatus for ART based on plan library invoking provided in an embodiment of this application, the first acquisition unit 601 acquires the medical image of the day and the target plan library of the target patient. The target plan library includes the plurality of groups of images of the target patient and the radiation therapy plan corresponding to each set of images. The determination unit 602 determines the radiation therapy plan corresponding to the target patient according to the medical image of the day and the target plan library. In this way, the problem that high-speed ART cannot be achieved due to excessive time consumption during the designing of the radiation therapy plan in the related art is resolved. Through the medical image of the day of the target patient and in view of the target plan library of the target patient, the radiation therapy plan of this radiation therapy for the target patient may be directly determined, so that an effect of the high-speed ART for the target patient can be achieved.

Optionally, in the apparatus for ART based on plan library invoking provided in an embodiment of this application, the acquisition unit includes a determination module, a registration module, and an updating module. The determination module is configured to determine whether there is an offline plan library corresponding to the target patient. The offline plan library includes a plurality of groups of images of the target patient and a radiation therapy plan corresponding to each set of images. The registration module is configured to, when there is the offline plan library corresponding to the target patient, perform image registration on the medical image of the day and the plurality of groups of images in the offline plan library to obtain a deformation field. The updating module is configured to, when a deformation quantity of the deformation field is less than a preset threshold I, use the offline plan library as the target plan library, or update the radiation therapy plan of the offline plan library according to the deformation quantity to obtain the target plan library.

Optionally, in the apparatus for ART based on plan library invoking provided in an embodiment of this application, the apparatus further includes a first construction unit. The first construction unit is configured to, when there is no offline plan library corresponding to the target patient, or the deformation quantity of the deformation field is greater than or equal to the preset threshold I, construct the target plan library of the target patient based on a data set of the medical image of the day.

Optionally, in the apparatus for ART based on plan library invoking provided in an embodiment of this application, the construction unit includes a first acquisition module, a generation module, and an adoption module. The first acquisition module is configured to acquire the plurality of groups of images of the target patient from the data set of the medical image of the day. The generation module is configured to generate an initial radiation therapy plan corresponding to each set of images. The adoption module is configured to perform checking and verification on the initial radiation therapy plan, and construct the target plan library by using the checked and verified initial radiation therapy plan.

Optionally, in the apparatus for ART based on plan library invoking provided in an embodiment of this application, the apparatus further includes a second acquisition unit, a second construction unit, and a correction unit. The second acquisition unit is configured to, before the radiation therapy plan corresponding to the target patient is determined according to the medical image of the day and the target plan library, acquire a motion time sequence data set of the target patient. The motion time sequence data set includes at least a body surface feature motion time sequence of the target patient or an in vivo feature motion time sequence of the target patient. The second construction unit is configured to construct a trajectory prediction model according to the motion time sequence data set. The trajectory prediction model is configured to perform trajectory prediction on a region of interest of the target patient. The correction unit is configured to perform delay correction on the trajectory prediction model to obtain a target trajectory prediction model.

Optionally, in the apparatus for ART based on plan library invoking provided in an embodiment of this application, the determination unit includes a prediction module, a second acquisition module, a comparison module, and a first determination module. The prediction module is configured to predict position information of the region of interest after preset time according to the target trajectory prediction model to obtain the predicted position information. The second acquisition module is configured to acquire a radiation therapy plan I matching the predicted position information from the target plan library. The comparison module is configured to perform contrastive analysis on the predicted position information and real-time position information of the region of interest to obtain a difference value. The first determination module is configured to, when the difference value is less than a preset threshold II, use the radiation therapy plan I as the radiation therapy plan corresponding to the target patient.

Optionally, in the apparatus for ART based on plan library invoking provided in an embodiment of this application, the determination unit further includes a matching module, a third acquisition module, and a second determination module. The matching module is configured to match the plurality of groups of images in the target plan library according to the medical image of the day to obtain a target image. The third acquisition module is configured to acquire a radiation therapy plan corresponding to the target image. The second determination module is configured to use the radiation therapy plan corresponding to the target image as the radiation therapy plan corresponding to the target patient.

The apparatus for ART based on plan library invoking includes a processor and a memory. The first acquisition unit 601 and the determination unit 602 are all stored in the memory as program units, and the processor executes the program units stored in the memory to implement corresponding functions.

The processor includes a kernel, and the kernel invokes the corresponding program units from the memory. There may be one or more kernels arranged. An ART plan for the target patient is implemented by adjusting kernel parameters.

The memory may include a non-persistent memory in a computer-readable medium, a Random Access Memory (RAM), and/or a non-volatile memory, for example, a Read Only Memory (ROM) or a flash memory (flash RAM). The memory includes at least one memory chip.

An embodiment of this application provides a computer-readable storage medium. The computer-readable storage medium stores a program. The method for ART based on plan library invoking is implemented when the program is performed by the processor.

An embodiment of this application provides a processor. The processor is configured to operate a program. When the program is operated, the method for ART based on plan library invoking is performed.

An embodiment of this application provides a device. The device includes a processor, a memory, and a program stored on the memory and executable on the processor. When the processor executes the program, the following steps of acquiring a medical image of the day and a target plan library of a target patient, where the target plan library comprises a plurality of groups of images of the target patient and a radiation therapy plan corresponding to each set of images; and determining the radiation therapy plan corresponding to the target patient according to the medical image of the day and the target plan library are implemented.

Optionally, the acquiring a medical image of the day and a target plan library of a target patient includes: determining whether there is an offline plan library corresponding to the target patient, where the offline plan library comprises a plurality of groups of images of the target patient and a radiation therapy plan corresponding to each set of images; when there is the offline plan library corresponding to the target patient, performing image registration on the medical image of the day and the plurality of groups of images in the offline plan library to obtain a deformation field; and when a deformation quantity of the deformation field is less than a preset threshold I, using the offline plan library as the target plan library, or updating the radiation therapy plan of the offline plan library according to the deformation quantity to obtain the target plan library.

Optionally, the method further includes: when there is no offline plan library corresponding to the target patient, or the deformation quantity of the deformation field is greater than or equal to the preset threshold I, constructing the target plan library of the target patient based on a data set of the medical image of the day.

Optionally, the constructing the target plan library of the target patient based on a data set of the medical image of the day includes: acquiring the plurality of groups of images of the target patient from the data set of the medical image of the day; generating an initial radiation therapy plan corresponding to each set of images; and performing checking and verification on the initial radiation therapy plan, and constructing the target plan library by using the checked and verified initial radiation therapy plan.

Optionally, before the determining the radiation therapy plan corresponding to the target patient according to the medical image of the day and the target plan library, the method further includes: acquiring a motion time sequence data set of the target patient, where the motion time sequence data set includes at least a body surface feature motion time sequence of the target patient or an in vivo feature motion time sequence of the target patient; constructing a trajectory prediction model according to the motion time sequence data set, where the trajectory prediction model is configured to perform trajectory prediction on a region of interest of the target patient; and performing delay correction on the trajectory prediction model to obtain a target trajectory prediction model.

Optionally, the determining the radiation therapy plan corresponding to the target patient according to the medical image of the day and the target plan library includes: predicting position information of the region of interest after preset time according to the target trajectory prediction model to obtain the predicted position information; acquiring a radiation therapy plan I matching the predicted position information from the target plan library; performing contrastive analysis on the predicted position information and real-time position information of the region of interest to obtain a difference value; and when the difference value is less than a preset threshold II, using the radiation therapy plan I as the radiation therapy plan corresponding to the target patient.

Optionally, the determining the radiation therapy plan corresponding to the target patient according to the medical image of the day and the target plan library includes: matching the plurality of groups of images in the target plan library according to the medical image of the day to obtain a target image; acquiring a radiation therapy plan corresponding to the target image; and using the radiation therapy plan corresponding to the target image as the radiation therapy plan corresponding to the target patient. The device herein may be a server, a PC, a PAD, a mobile phone, or the like.

This application further provides a computer program product. When being performed on a data processing device, the computer program product adapts to perform a program initialized with the following method steps: acquiring a medical image of the day and a target plan library of a target patient, where the target plan library comprises a plurality of groups of images of the target patient and a radiation therapy plan corresponding to each set of images; and determining the radiation therapy plan corresponding to the target patient according to the medical image of the day and the target plan library.

Optionally, the acquiring a medical image of the day and a target plan library of a target patient includes: determining whether there is an offline plan library corresponding to the target patient, where the offline plan library comprises a plurality of groups of images of the target patient and a radiation therapy plan corresponding to each set of images; when there is the offline plan library corresponding to the target patient, performing image registration on the medical image of the day and the plurality of groups of images in the offline plan library to obtain a deformation field; and when a deformation quantity of the deformation field is less than a preset threshold I, using the offline plan library as the target plan library, or updating the radiation therapy plan of the offline plan library according to the deformation quantity to obtain the target plan library.

Optionally, the method further includes: when there is no offline plan library corresponding to the target patient, or the deformation quantity of the deformation field is greater than or equal to the preset threshold I, constructing the target plan library of the target patient based on the medical image of the day.

Optionally, the constructing the target plan library of the target patient based on a data set of the medical image of the day includes: acquiring the plurality of groups of images of the target patient from the data set of the medical image of the day; generating an initial radiation therapy plan corresponding to each set of images; and performing checking and verification on the initial radiation therapy plan, and constructing the target plan library by using the checked and verified initial radiation therapy plan.

Optionally, before the determining the radiation therapy plan corresponding to the target patient according to the medical image of the day and the target plan library, the method further includes: acquiring a motion time sequence data set of the target patient, where the motion time sequence data set includes at least a body surface feature motion time sequence of the target patient or an in vivo feature motion time sequence of the target patient; constructing a trajectory prediction model according to the motion time sequence data set, where the trajectory prediction model is configured to perform trajectory prediction on a region of interest of the target patient; and performing delay correction on the trajectory prediction model to obtain a target trajectory prediction model.

Optionally, the determining the radiation therapy plan corresponding to the target patient according to the medical image of the day and the target plan library includes: predicting position information of the region of interest after preset time according to the target trajectory prediction model to obtain the predicted position information; acquiring a radiation therapy plan I matching the predicted position information from the target plan library; performing contrastive analysis on the predicted position information and real-time position information of the region of interest to obtain a difference value; and when the difference value is less than a preset threshold II, using the radiation therapy plan I as the radiation therapy plan corresponding to the target patient.

Optionally, the determining the radiation therapy plan corresponding to the target patient according to the medical image of the day and the target plan library includes: matching the plurality of groups of images in the target plan library according to the medical image of the day to obtain a target image; acquiring a radiation therapy plan corresponding to the target image; and using the radiation therapy plan corresponding to the target image as the radiation therapy plan corresponding to the target patient.

Those skilled in the art should understand that the embodiments of this application may be provided as a method, a system, or a computer program product. Therefore, this application may adopt forms of complete hardware embodiments, complete software embodiments or embodiments integrating software and hardware. Moreover, this application may adopt the form of a computer program product implemented on one or more computer available storage media (including but being not limited to a disk memory, a Compact Disc Read Only Memory (CD-ROM), an optical memory, and the like) containing computer available program codes.

This application is described with reference to flowcharts and/or block diagrams of the method, the device (system) and the computer program product according to the embodiments of this application. It should be understood that each flow and/or block in the flowchart and/or block diagram, and the combination of the flow and/or block in the flowchart and/or block diagram can be implemented by the computer program instructions. These computer program instructions can be provided to a processor of a general-purpose computer, a special-purpose computer, an embedded processor or other programmable data processing devices to generate a machine, so that instructions which are executed by the processor of the computer or other programmable data processing devices generate a device which is used for implementing the specified functions in one or more flows of the flowchart and/or one or more blocks of the block diagram.

These computer program instructions may also be stored in the computer-readable memory which can guide the computer or other programmable data processing devices to work in a particular way, so that the instructions stored in the computer-readable memory generate a product including an instruction device. The instruction device implements the specified functions in one or more flows of the flowchart and/or one or more blocks of the block diagram.

These computer program instructions may also be loaded on the computer or other programmable data processing devices, so that a series of operation steps are performed on the computer or other programmable data processing devices to generate the processing implemented by the computer, and the instructions executed on the computer or other programmable data processing devices provide the steps for implementing the specified functions in one or more flows of the flowchart and/or one or more blocks of the block diagram.

In a typical configuration, a computing device includes one or more processors (CPUs), an input/output interface, a network interface, and an internal memory.

The memory may include a non-persistent memory in a computer-readable medium, a Random Access Memory (RAM) and/or a non-volatile memory, for example, a Read Only Memory (ROM) or a flash memory (flash RAM). The memory is an example of the computer-readable medium.

The computer-readable medium includes both persistent and non-permanent, removable and non-removable media, and may achieve information storage by any method or technology. The information may be a computer-readable instruction, a data structure, a module of a program, or other data. Examples of a computer storage medium include but are not limited to a Phase Change Memory (PRAM), a Static Random Access Memory (SRAM), a Dynamic Random Access Memory (DRAM), other types of Random Access Memories (RAM), a Read-Only Memory (ROM), an Electrically Erasable Programmable Read-Only Memory (EEPROM), a flash memory or other memory technologies, a Compact Disk Read-Only Memory (CD-ROM), a Digital Versatile Disc (DVD) or other optical storages, a cartridge storage, a magnetic tape disk storage or other magnetic storage devices or any other non-transmitting medium that may be configured to store information accessible by a computing device. According to the definition herein, the computer-readable medium does not include transitory computer-readable media, such as modulated data signals and carriers.

It is also to be noted that, terms "comprise", "include" or any other variants are intended to encompass non-exclusive inclusion, such that a process, a method, a commodity, or a device including a series of elements not only include those elements, but also includes other elements not listed explicitly or includes intrinsic elements for the process, the method, the commodity, or the device. Without any further limitation, an element defined by the phrase "comprising one" does not exclude existence of other same elements in the process, the method, the commodity, or the device that includes the elements.

Those skilled in the art should understand that the embodiments of this application may be provided as a method, a system, or a computer program product. Therefore, this application may adopt forms of complete hardware embodiments, complete software embodiments or embodiments integrating software and hardware. Moreover, this application may adopt the form of a computer program product implemented on one or more computer available storage media (including but being not limited to a disk memory, a Compact Disc Read Only Memory (CD-ROM), an optical memory, and the like) containing computer available program codes.

The above are only the preferred embodiments of this application and are not intended to limit this application. For those skilled in the art, this application may have various modifications and variations. Any modifications, equivalent replacements, improvements and the like made within the spirit and principle of this application shall fall within the scope of claims of this application.

What is claimed is:

1. A method for Adaptive Radiation Therapy (ART) based on plan library invoking, comprising:
   acquiring a medical image of the day and a target plan library of a target patient, wherein the target plan library comprises a plurality of groups of images of the target patient and a radiation therapy plan corresponding to each set of images; and
   determining the radiation therapy plan corresponding to the target patient according to the medical image of the day and the target plan library;
   wherein the acquiring a medical image of the day and a target plan library of a target patient comprises:
   determining whether there is an offline plan library corresponding to the target patient, wherein the offline plan library comprises a plurality of groups of images of the target patient and a radiation therapy plan corresponding to each set of images;
   when there is the offline plan library corresponding to the target patient, performing image registration on the medical image of the day and the plurality of groups of images in the offline plan library to obtain a deformation field; and
   when a deformation quantity of the deformation field is less than a preset threshold I, using the offline plan library as the target plan library, or updating the radiation therapy plan of the offline plan library according to the deformation quantity to obtain the target plan library.

2. The method according to claim 1, further comprising:
   when there is no offline plan library corresponding to the target patient, or the deformation quantity of the deformation field is greater than or equal to the preset threshold I, constructing the target plan library of the target patient based on a data set of the medical image of the day.

3. The method according to claim 2, wherein the constructing the target plan library of the target patient based on a data set of the medical image of the day comprises:
   acquiring the plurality of groups of images of the target patient from the data set of the medical image of the day;

generating an initial radiation therapy plan corresponding to each set of images; and performing checking and verification on the initial radiation therapy plan, and constructing the target plan library by using the checked and verified initial radiation therapy plan.

4. The method according to claim 3, wherein, before the determining the radiation therapy plan corresponding to the target patient according to the medical image of the day and the target plan library, the method further comprises:

acquiring a motion time sequence data set of the target patient, wherein the motion time sequence data set comprises at least a body surface feature motion time sequence of the target patient or an in vivo feature motion time sequence of the target patient;

constructing a trajectory prediction model according to the motion time sequence data set, wherein the trajectory prediction model is configured to perform trajectory prediction on a region of interest of the target patient; and performing delay correction on the trajectory prediction model to obtain a target trajectory prediction model.

5. The method according to claim 4, wherein, the determining the radiation therapy plan corresponding to the target patient according to the medical image of the day and the target plan library comprises:

predicting position information of the region of interest after preset time according to the target trajectory prediction model to obtain the predicted position information;

acquiring a radiation therapy plan I matching the predicted position information from the target plan library;

performing contrastive analysis on the predicted position information and real-time position information of the region of interest to obtain a difference value; and when the difference value is less than a preset threshold II, using the radiation therapy plan I as the radiation therapy plan corresponding to the target patient.

6. The method according to claim 1, wherein, the determining the radiation therapy plan corresponding to the target patient according to the medical image of the day and the target plan library comprises:

matching the plurality of groups of images in the target plan library according to the medical image of the day to obtain a target image;

acquiring a radiation therapy plan corresponding to the target image; and using the radiation therapy plan corresponding to the target image as the radiation therapy plan corresponding to the target patient.

7. A non-transitory computer-readable storage medium, storing a program, wherein the program performs the method for Adaptive Radiation Therapy (ART) based on plan library invoking according to claim 1.

8. A processor, configured to operate a program, wherein the method for Adaptive Radiation Therapy (ART) based on plan library invoking according to claim 1 is performed when the program is operated.

9. An apparatus for Adaptive Radiation Therapy (ART), comprising:

a first acquisition unit, configured to acquire a medical image of the day and a target plan library of a target patient, wherein the target plan library comprises a plurality of groups of images of the target patient and a radiation therapy plan corresponding to each set of images; and a determination unit, configured to determine the radiation therapy plan corresponding to the target patient according to the medical image of the day and the target plan library;

wherein the acquisition unit includes a determination module, a registration module, and an updating module;

the determination module, configured to determine whether there is an offline plan library corresponding to the target patient;

the offline plan library includes a plurality of groups of images of the target patient and a radiation therapy plan corresponding to each set of images;

the registration module, configured to, when there is the offline plan library corresponding to the target patient, perform image registration on the medical image of the day and the plurality of groups of images in the offline plan library to obtain a deformation field;

the updating module, configured to, when a deformation quantity of the deformation field is less than a preset threshold I, use the offline plan library as the target plan library, or update the radiation therapy plan of the offline plan library according to the deformation quantity to obtain the target plan library.

* * * * *